US010111879B2

(12) United States Patent
Tagliati et al.

(10) Patent No.: US 10,111,879 B2
(45) Date of Patent: Oct. 30, 2018

(54) ADRENOCEPTORS ANTAGONISTS FOR THE PREVENTION AND TREATMENT OF NEURODEGENERATIVE CONDITIONS

(71) Applicant: Cedars-Sinai Medical Center, Los Angeles, CA (US)

(72) Inventors: Michele Tagliati, Pacific Palisades, CA (US); Gennaro Pagano, Napoli (IT)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 14/900,315

(22) PCT Filed: Jun. 27, 2014

(86) PCT No.: PCT/US2014/044715
§ 371 (c)(1),
(2) Date: Dec. 21, 2015

(87) PCT Pub. No.: WO2014/210544
PCT Pub. Date: Dec. 31, 2014

(65) Prior Publication Data
US 2016/0324862 A1  Nov. 10, 2016

Related U.S. Application Data

(60) Provisional application No. 61/840,381, filed on Jun. 27, 2013.

(51) Int. Cl.
*A61K 31/5377* (2006.01)
*A61K 31/138* (2006.01)
*A61K 31/167* (2006.01)
*A61K 31/198* (2006.01)
*A61K 31/403* (2006.01)
*A61K 31/404* (2006.01)
*A61B 6/00* (2006.01)
*A61K 45/06* (2006.01)

(52) U.S. Cl.
CPC ........ *A61K 31/5377* (2013.01); *A61K 31/138* (2013.01); *A61K 31/167* (2013.01); *A61K 31/198* (2013.01); *A61K 31/403* (2013.01); *A61K 31/404* (2013.01); *A61K 45/06* (2013.01); *A61B 6/507* (2013.01)

(58) Field of Classification Search
CPC .... A61B 6/507; A61K 31/138; A61K 31/167; A61K 31/198; A61K 31/403; A61K 31/5377; A61K 31/404; A61K 45/06
See application file for complete search history.

(56) References Cited

U.S. PATENT DOCUMENTS

| 6,203,776 B1 * | 3/2001 | Bristow | G01N 33/566 424/1.11 |
|---|---|---|---|
| 6,358,990 B1 | 3/2002 | Howlett et al. | |
| 2003/0096829 A1 | 5/2003 | Li et al. | |
| 2004/0110826 A1 | 6/2004 | Uesaka et al. | |
| 2004/0248984 A1 | 12/2004 | Krieglstein et al. | |
| 2005/0143378 A1 | 6/2005 | Yun et al. | |
| 2007/0021421 A1 | 1/2007 | Hampton | |
| 2007/0281906 A1 | 12/2007 | Dalton et al. | |
| 2008/0076828 A1 | 3/2008 | Dalton et al. | |
| 2009/0143279 A1 | 6/2009 | Mootha et al. | |
| 2009/0215852 A1 | 8/2009 | Bascomb et al. | |
| 2010/0029620 A1 | 2/2010 | Andres-Gil et al. | |
| 2010/0105694 A1 | 4/2010 | Andres-Gil et al. | |
| 2013/0053368 A1 | 2/2013 | Ruggero et al. | |

FOREIGN PATENT DOCUMENTS

| EP | 3013342 A2 | 5/2016 | |
|---|---|---|---|
| JP | 2010-525018 A | 7/2010 | |
| JP | 2012-92127 A | 5/2012 | |
| JP | 2016523918 A | 8/2016 | |
| KR | 20160026897 A | 3/2016 | |
| WO | WO-2009152521 A2 * | 12/2009 | ......... A61B 5/02405 |
| WO | 2012083128 A2 | 6/2012 | |
| WO | 2014210544 A2 | 12/2014 | |

OTHER PUBLICATIONS

Kashihara et. al., Journal of Neurology, 2006, European Neurological Society, vol. 253, suppl. 3, pp. 35-40.*
Postuma et. al., Movement Disorders, 2012, Wiley Online Library, vol. 27(5), pp. 617-626.*
Orimo et. al., Brain Pathology, 2007, International Society of Neuropathology, vol. 17, pp. 24-30.*
Carpentier, A.F. et al., Improvement of levodopa-induced dyskinesia by propranolol in Parkinson's disease, Neurology, 1996, 46:1548-1551.
Crosby, N.J. et al., Beta-blocker therapy for tremor in Parkinson's disease, Cochrane Database of Systematic Reviews, 2003, Issue 1 Art. No. CD003361, DOI: 1002/14651858.CD003361.
Foster, N.L. et al., Treatment of resting tremor by beta-adrenergic blockade, Am Heart J, 1984, 108:1173-1177.
Hughes, A.J. et al., Accuracy of clinical diagnosis of idiopathic Parkinson's disease: a clinico-pathological study of 100 cases, Journal of Neurology, Neurosurgery, and Psychiatry, 1992, 55:181-184.
Lees, A.J. et al., Parkinson's disease, Lancet, 2009, 373:2055-2066.
Lewitt, P.A. et al., Randomized clinical trial of fipamezole for dyskinesia in Parkinson's disease (FJORD study), Neurology, 2012, 79:163-169.

(Continued)

*Primary Examiner* — Sarah Pihonak
(74) *Attorney, Agent, or Firm* — Linda B. Huber; Nixon Peabody LLP

(57) ABSTRACT

The present disclosure teaches methods for treating and preventing a variety of neurodegenerative conditions and symptoms associated therewith, including Alzheimer's disease (AD) and idiopathic Parkinson's disease (iPD), by utilizing adrenoceptor antagonists. Adrenoceptor antagonists that can be used include β-blockers, such as acebutolol, betaxolol, bisopropolol, bopindolol, carvedilol, metoprolol, oxprenolol, propranolol, and timolol. The present disclosure also teaches methods for diagnosing and monitoring the progression of iPD.

14 Claims, 4 Drawing Sheets

(56) References Cited

OTHER PUBLICATIONS

Lim, S-Y et al., The nonmotor symptom of Parkinson's disease—an overview, Movement Disorder, 2010, 25(Suppl 1):S123-S130.
Oka, H. et al., Reduced cardiac 123I-MIBG uptake reflects cardiac sympathetic dysfunction in de novo Parkinson's disease, J. Neural Transm, 2011, 118:1323-1327.
Rascal, O. et al., Idazoxan, an alpha-2 antagonist, and L-DOPA-induced dyskinesias in patients with Parkinson's disease, Movement Disorders, 2001, 16(4):708-713.
Savica, R. et al., When does Parkinson disease start?, Arch Neural, 2010, 67(7):798-801.
Wolters, E. Ch. et al., Parkinson's disease: premotor clinico-pathological correlations, J Neural Transm, 2006, Suppl, 70:309-319.
International Search Report and Written Opinion dated Dec. 16, 2014 for International Application No. PCT/US14/44715 filed Jun. 27, 2014, 13 pages.
De Milliano et al. Metoprolol-induced changes in myocardial (123)I-metaiodobenzylguanidine uptake in Parkinson's disease. Circulation (2000). 102(20):2553-4.
Goldstein et al. Sympathetic Cardioneuropathy in Dysautonomias. N Engl J Med (1997). 336(10):696-702.
Orimo et al. (123)I-metaiodobenzylguanidine myocardial scintigraphy in Parkinson's disease. J Neurol Neurosurg Psychiatry (1999). 67(2):189-94.
Spiegel. Diagnostic and Pathophysiological Impact of Myocardial MIBG Scintigraphy in Parkinson's Disease. Parkinson's Disease (2010). 6 pages.
EP Application No. 14818416.1 Partial supplementary European search report dated Oct. 24, 2016; 9 pages.
Coenen et al. Noradrenergic modulation of subthalamic nucleus activity in human: metoprolol reduces spiking activity in microelectrode recordings during deep brain stimulation surgery for Parkinson's disease. Acta Neurochir (Wien) (2008). 150:757-762.
Wang et al. Carvedilol as a potential novel agent for the treatment of Alzheimer's disease. Neurobiology of Aging (2011). 32:2321. e2-2321.e12.
EP 14818416.1 Extended Search Report dated Feb. 1, 2017, 10 pages.
Hawkes et al., A Timeline for Parkinson's Disease, Parkinsonism and Related Disorders, 2010, vol. 16, pp. 79-84.
Circulation Journal, 2007, vol. 71, Supplement 3, 52 in p. 951.
Hamada et al., Onset Age and Severity of Motor Impairment Are Associated with Reduction of Myocardio I-MIBG Uptake in Parkinson's Disease, 2003, J. Neurol. Neurosurg. Psychiatry, vol. 74, pp. 423-426.
Takatsu et al., Cardiac Sympathetic Denervation from the Early Stage of Parkinson's Disease: Clinical and Experimental Studies with Radiolabeled MIBG, 2000, The Journal of Nuclear Medicine, vol. 41(1), pp. 71-77.

\* cited by examiner

ADRENOCEPTORS ANTAGONISTS FOR THE PREVENTION AND TREATMENT OF NEURODEGENERATIVE CONDITIONS

CROSS REFERENCE TO RELATED APPLICATION

This application is a National Phase of International Application No. PCT/US2014/044715, filed Jun. 27, 2014, currently pending, which designated the U.S. and that International Application was published under PCT Article 21(2) in English, which claims priority under 35 U.S.C. § 119(e) to U.S. Provisional Application No. 61/840,381, filed Jun. 27, 2013, the contents of which are herein incorporated by reference in their entirety.

FIELD OF THE INVENTION

The present invention generally relates to the prevention and treatment of neurodegenerative conditions.

BACKGROUND

The following description includes information that may be useful in understanding the present invention. It is not an admission that any of the information provided herein is prior art or relevant to the presently claimed invention.

Idiopathic Parkinson's disease (iPD) is a progressive disorder for which there is no known treatment capable of effectively slowing down or stopping disease progression. While symptomatic treatment of iPD is possible, it is based mainly on dopaminergic supplementation, which only temporarily improves motor impairment and quality of life.

There is clearly a need for new treatments for iPD (and related neurodegenerative diseases) that alleviate the symptoms while also addressing the underlying cause. There is also a need for methods of diagnosing iPD at an early stage, and monitoring its progression.

SUMMARY OF THE INVENTION

In various embodiments, the invention teaches a method for alleviating the symptoms of and/or slowing the progression of a neurodegenerative condition in a subject. In some embodiments, the method includes providing a therapeutically effective amount of a composition comprising an adrenoceptor antagonist to the subject. In certain embodiments, the neurodegenerative condition is selected from the group consisting of idiopathic Parkinson's disease (iPD), Dementia with Lewy Bodies (DLB), Multiple System Atrophy (MSA), Pure Autonomic Failure (PAF), Alzheimer's disease (AD), Progressive Supranuclear Palsy (PSP), Cortico-Basal Degeneration (CBD), and Huntington's Disease (HD). In some embodiments, the neurodegenerative condition is idiopathic Parkinson's disease (iPD). In some embodiments, the adrenoceptor antagonist is an antagonist of a receptor selected from the group consisting of: $\alpha 1$, $\alpha 2$, $\beta 1$, $\beta 2$, and combinations thereof. In some embodiments, the adrenoceptor antagonist is a $\beta$-blocker. In some embodiments, the composition has L-type calcium channel blocking activity. In some embodiments, the method includes providing a therapeutically effective amount of an L-type calcium channel blocker to the subject. In certain embodiments, the composition used in the inventive method includes a drug selected from the group consisting of: acebutolol, betaxolol, bisopropolol, bopindolol, carvedilol, metoprolol, oxprenolol, propranolol, and timolol. In some embodiments, the method further includes providing a composition comprising a dopaminergic agent to the subject. In certain embodiments, the subject is a mammal. In some embodiments, the subject is a human. In certain embodiments, one of the symptoms is constipation.

In various embodiments, the invention teaches a method for preventing a neurodegenerative condition in a subject, including providing a prophylactically effective amount of a composition including an adrenoceptor antagonist to the subject. In certain embodiments, the neurodegenerative condition is selected from the group consisting of: idiopathic Parkinson's disease (iPD), Dementia with Lewy Bodies (DLB), Multiple System Atrophy (MSA), Pure Autonomic Failure (PAF), Alzheimer's disease (AD), Progressive Supranuclear Palsy (PSP), Cortico-Basal Degeneration (CBD), and Huntington's Disease (HD). In certain embodiments, the neurodegenerative condition is idiopathic Parkinson's disease (iPD). In some embodiments, the adrenoceptor antagonist is an antagonist of a receptor selected from the group consisting of: $\alpha 1$, $\alpha 2$, $\beta 1$, $\beta 2$, and combinations thereof. In certain embodiments, the adrenoceptor antagonist is a $\beta$-blocker. In some embodiments, the composition includes a drug having L-type calcium channel blocking activity. In some embodiments, the invention includes providing a therapeutically effective amount of an L-type calcium channel blocker to the subject. In certain embodiments, the method includes providing a dopaminergic agent to the subject. In some embodiments, the composition used in the method includes a drug selected from the group consisting of: acebutolol, betaxolol, bisopropolol, bopindolol, carvedilol, metoprolol, oxprenolol, propranolol, and timolol. In some embodiments, the subject is a mammal. In certain embodiments, the subject is a human.

In various embodiments, the invention teaches a method for determining whether or not idiopathic Parkinson's disease (iPD) is progressing in a subject, including: (1) performing an initial assay to measure cardiac uptake of iodine-123-metaiodobenzylguanidine ($^{123}$I-MIBG) in a subject suspected of having, or having been diagnosed with, iPD; and (2) subsequently performing an additional assay to measure cardiac uptake of $^{123}$I-MIBG in the subject, wherein it is determined iPD is progressing in the subject if the cardiac uptake of $^{123}$I-MIBG has decreased in the additional assay, compared to the initial assay; and wherein it is determined iPD is not progressing in the subject if the cardiac uptake of $^{123}$I-MIBG has not decreased in the additional assay, compared to the initial assay. In some embodiments, the cardiac uptake of $^{123}$I-MIBG is measured by $^{123}$I-MIBG myocardial scintigraphy. In certain embodiments, a composition including one or more adrenoceptor antagonist is administered to the subject in the time between the initial and subsequent assay, and the adrenoceptor antagonist is selected from the group consisting of: acebutolol, betaxolol, bisopropolol, bopindolol, carvedilol, metoprolol, oxprenolol, propranolol, and timolol.

In various embodiments, the invention teaches a method for diagnosing a subject with the presence or absence of idiopathic Parkinson's disease (iPD), including: performing an assay to measure cardiac uptake of iodine-123-metaiodobenzylguanidine ($^{123}$I-MIBG) in a subject suspected of having iPD, and diagnosing the subject as having iPD if the cardiac uptake of $^{123}$I-MIBG is less than that of a subject who does not have iPD, and diagnosing the subject as not having iPD, if the cardiac uptake of $^{123}$I-MIBG is not less than that of a subject who does not have iPD. In some embodiments, the cardiac uptake of $^{123}$I-MIBG is measured by $^{123}$I-MIBG myocardial scintigraphy.

In various embodiments, the invention teaches a kit for preventing, treating, or slowing the progression of a neurodegenerative condition in a subject. In certain embodiments, the kit includes a composition including an adrenoceptor antagonist; and instructions for the use thereof to prevent, treat, or slow the progression of a neurodegenerative condition. In certain embodiments, the neurodegenerative condition is selected from the group consisting of idiopathic Parkinson's disease (iPD), Dementia with Lewy Bodies (DLB), Multiple System Atrophy (MSA), Pure Autonomic Failure (PAF), Alzheimer's disease (AD), Progressive Supranuclear Palsy (PSP), Cortico-Basal Degeneration (CBD), and Huntington's Disease (HD). In some embodiments, the neurodegenerative condition is idiopathic Parkinson's disease (iPD). In certain embodiments, the adrenoceptor antagonist is an antagonist of a receptor selected from the group consisting of: $\alpha 1$, $\alpha 2$, $\beta 1$, $\beta 2$, and combinations thereof. In certain embodiments, the adrenoceptor antagonist is a $\beta$-blocker. In some embodiments, the composition has L-type calcium channel blocking activity. In some embodiments, the kit further includes an L-type calcium channel blocker. In certain embodiments, the composition includes a drug selected from the group consisting of: acebutolol, betaxolol, bisopropolol, bopindolol, carvedilol, metoprolol, oxprenolol, propranolol, and timolol. In some embodiments, the kit further includes a dopaminergic agent.

BRIEF DESCRIPTION OF THE DRAWINGS

Exemplary embodiments are illustrated in the referenced figures. It is intended that the embodiments and figures disclosed herein are to be considered illustrative rather than restrictive.

DESCRIPTION OF THE INVENTION

Figure 1:
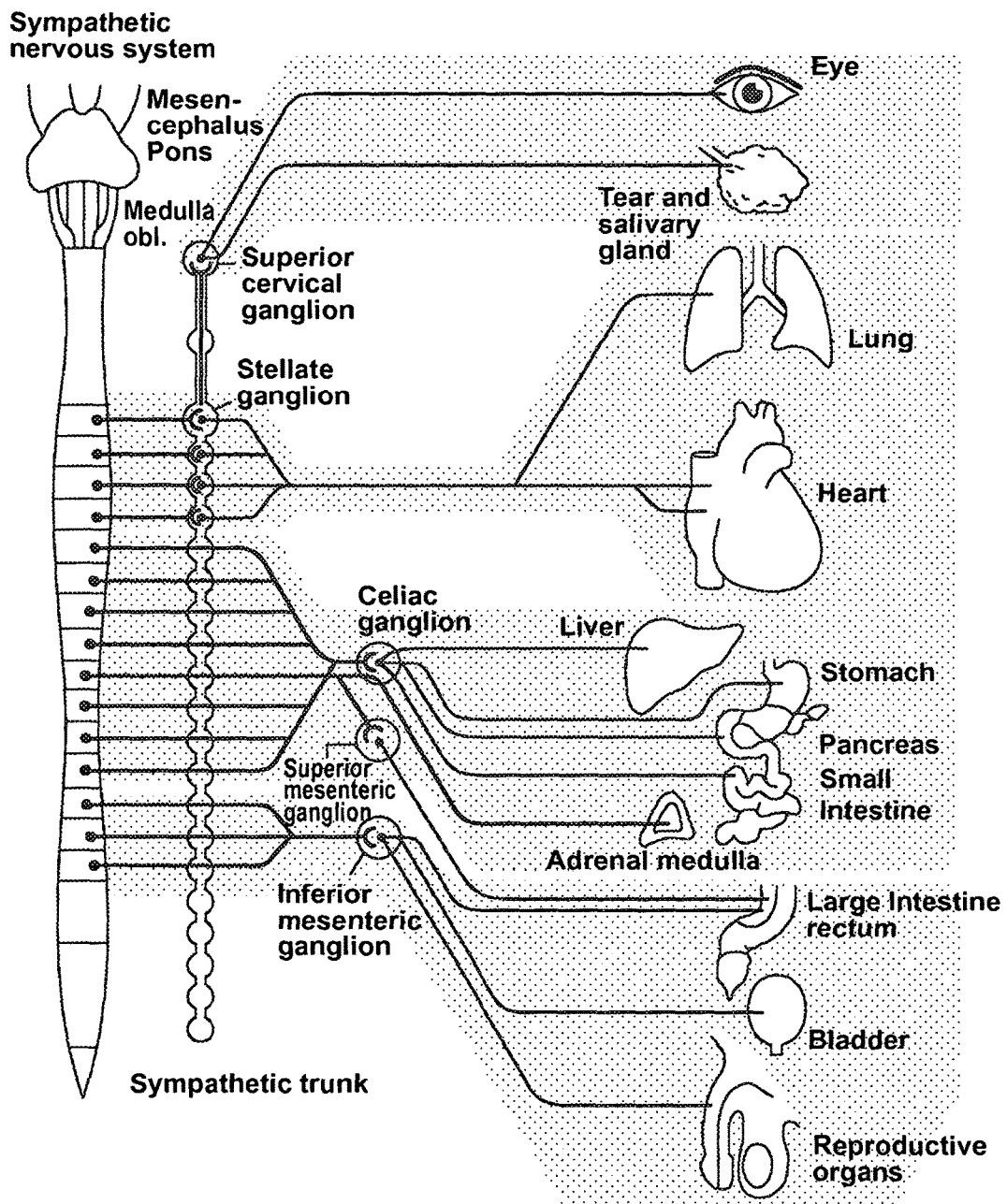
FIG. 1 demonstrates, in accordance with an embodiment of the invention, target organs of the sympathetic response to stress, mediated by the locus coeruleus and sympathetic nervous system.
Figure 2:
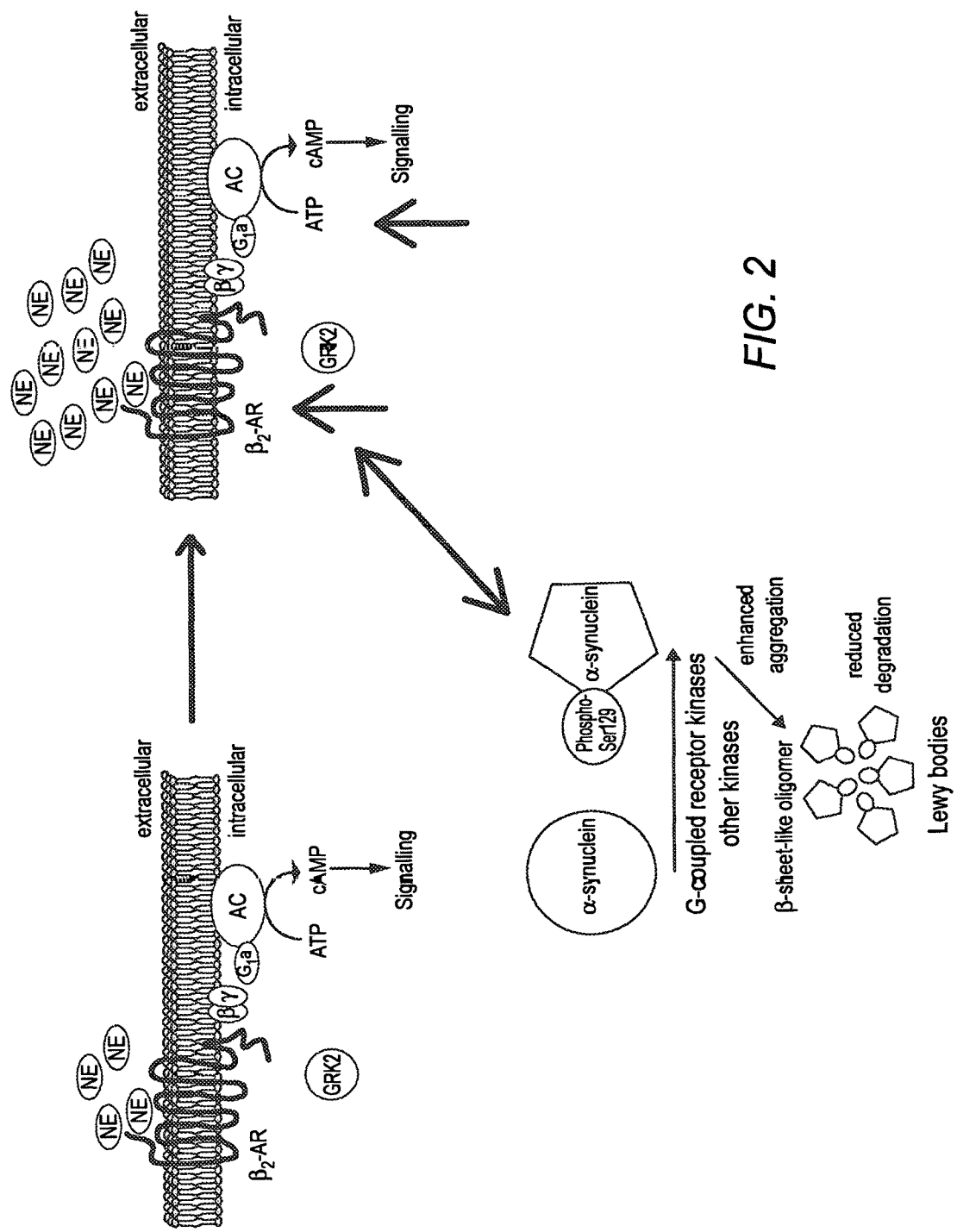
FIG. 2 demonstrates, in accordance with an embodiment of the invention, a diagram of the mechanism of abnormal $\alpha$-synuclein accumulation mediated by pathological activation of G-coupled receptor kinases (GRK) triggered by norepinephrine (NE) overstimulation.
Figure 3:
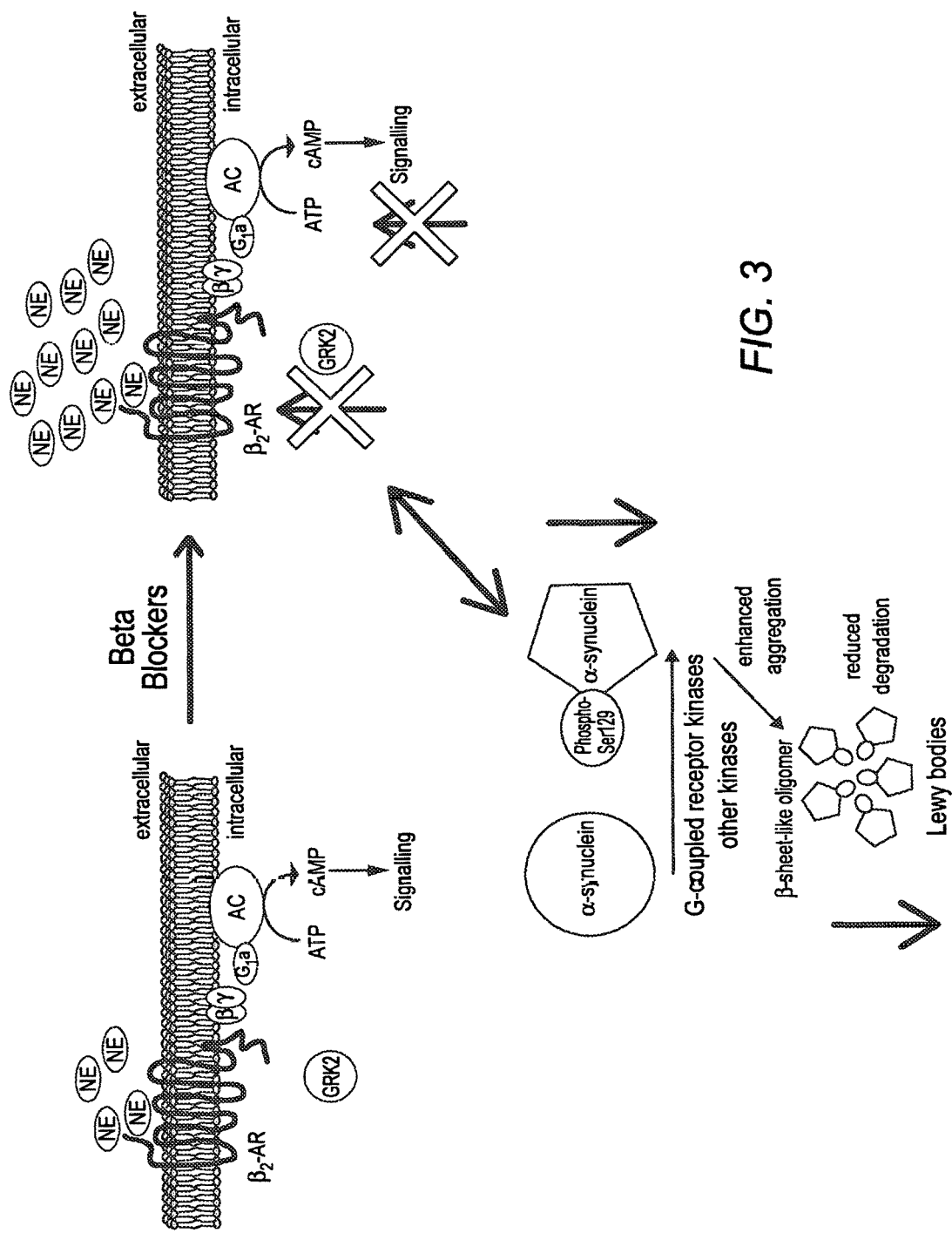
FIG. 3 demonstrates, in accordance with an embodiment of the invention, adrenergic receptor blockade slows down the pathological mechanism leading to $\alpha$-synuclein accumulation and progression of the disease.
Figure 4:
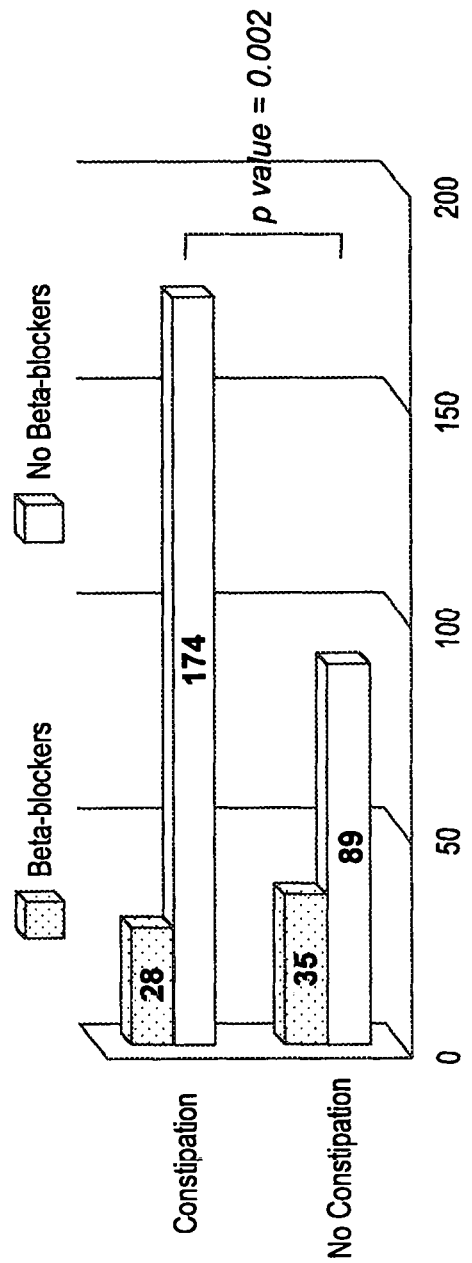
FIG. 4 demonstrates, in accordance with an embodiment of the invention, a graph indicating the influence of beta blocker treatment on constipation in patients with Parkinson's disease.

All references cited herein are incorporated by reference in their entirety as though fully set forth. Unless defined otherwise, technical and scientific terms used herein have the same meaning as commonly understood by one of ordinary skill in the art to which this invention belongs. March, *Advanced Organic Chemistry Reactions, Mechanisms and Structure* 5$^{th}$ ed.; and Guyton and Hall, *Textbook of Medical Physiology* 12$^{th}$ ed., provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

As used herein, "NE" is an acronym for norepinephrine.

As used herein, "E" is an abbreviation for epinephrine.

As used herein, "SNS" is an abbreviation for sympathetic nervous system.

As used herein, "iPD" is an acronym for idiopathic Parkinson's disease.

As used herein, "DLB" is an acronym for dementia with Lewy bodies.

As used herein, "MSA" is an acronym for multiple system atrophy.

As used herein, "PAF" is an acronym for pure autonomic failure.

As used herein, "AD" is an acronym for Alzheimer's disease.

As used herein, "PSP" is an acronym for progressive supranuclear palsy.

As used herein, "CBD" is an acronym for cortico-basal degeneration.

As used herein, "HD" is an acronym for Huntington's disease.

As used herein, "beneficial results" may include, but are in no way limited to, lessening or alleviating the severity of a disease condition, or symptoms associated therewith, preventing a disease condition from worsening, curing a disease condition, preventing a disease condition from developing, lowering the chances of a subject developing a disease condition, and prolonging a subject's life or life expectancy.

"Conditions," "disease conditions," and "neurodegenerative conditions," as used herein, may include but are in no way limited to iPD, DLB, MSA, PAF, AD, PSP, CBD, and HD.

"Mammal," as used herein, refers to any member of the class *Mammalia*, including, without limitation, humans and nonhuman primates such as chimpanzees and other apes and monkey species; farm animals such as cattle, sheep, pigs, goats and horses; domesticated mammals, such as dogs and cats; laboratory animals including rodents such as mice, rats and guinea pigs, and the like. The term does not denote a particular age or sex. Thus, adult and newborn subjects, whether male or female, are intended to be included within the scope of this term.

"Treatment" and "treating," as used herein, refer to both therapeutic treatment and prophylactic or preventative measures, wherein the object is to slow down (lessen) the neurodegenerative condition, prevent the neurodegenerative condition, pursue or obtain beneficial results, or lower the chances of the individual developing the neurodegenerative condition, even if the treatment is ultimately unsuccessful. Those in need of treatment include those already with the neurodegenerative condition, as well as those prone to have the condition or those in whom the condition is to be prevented.

In the embodiments described herein, in each instance in which the term "providing" is used with regard to the therapeutic compositions, the term "administering" is also contemplated. In other words, in every instance in which a composition is provided, it could alternatively be administered directly to the patient, and that is within the scope of the invention.

By way of background, $\beta$-adrenergic receptors are activated by NE and epinephrine (E). Cells in the central nervous system (CNS) which contain E stimulate the activation of the SNS. Experimental observations in laboratory animals revealed that the brain cells activating the SNS contain a substantial amount of neurotransmitter E, a neurotransmitter which potently activates β-adrenergic receptors.

Activation of the SNS increases alertness, attention, and energy, but excessive activation induces symptoms that parallel the typical pre-motor manifestations of iPD (constipation, sleep problems, anxiety, cardiac dysautonomia, anosmia, etc.). The inventors determined that chronic adrenoceptor activation could sustain the progression of disease, increasing the rate of α-synuclein aggregation. The inventors further determined that blockage of β-adrenergic receptors could relieve the clinical symptoms and reduce/revert the pathological mechanism leading to α-synuclein aggregation.

Motor symptoms could also improve with adrenoceptors modulation. Resting, postural, and action tremor in Parkinson's disease can be diminished by the β-adrenoceptor antagonist nadolol, and propranolol could reduce levodopa-induced dyskinesias without worsening Parkinsonism. Levodopa-induced dyskinesias could also be diminished by administration of α2-adrenergic receptor antagonists idazoxan and fipemazole, without a reduction in the anti-Parkinsonian benefits of levodopa.

Importantly, β-blockers acting to reduce these symptoms need to enter into the CNS by passage from the bloodstream across the blood-brain barrier, and there block β-adrenergic receptors hyperactivation. β-blockers that have been demonstrated to pass the blood-brain barrier, and could therefore be useful in the inventive method, include, but are in no way limited to: acebutolol, betaxolol, bisopropolol, bopindolol, carvedilol, metoprolol, oxprenolol, propranolol, and timolol.

Advantageously, carvedilol has several different effects on the adrenoceptors, including β-1 and β2 adrenergic blockade, α-1 adrenergic blockade, antioxidant activity, L-type calcium channel blockade, and inhibition of activation of stress-activated protein kinase. Therefore, carvedilol is particularly well-suited to block impaired sympathetic over-activation in early and advanced iPD. Absorption of current (oral) formulations of carvedilol is typically rapid and complete, with an average elimination half-life of about 8 hours. Carvedilol is ordinarily removed from the body in a two-part process, including liver and renal mechanisms. Some carvedilol liver metabolites could contribute to the beneficial effects. For example, the antioxidant activity of the carvedilol metabolite SB209995 has 50 to 100 times the potency of carvedilol and is 1000-fold more potent than vitamin E.

In view of all of the foregoing background and analysis, the inventors established a novel strategy (described in greater detail below) to treat or prevent a number of neurodegerative disorders and symptoms associated therewith.

In various embodiments, the invention teaches a method for preventing, slowing the progression of, or treating the symptoms of a neurodegenerative condition in a subject by providing a therapeutically effective amount of a composition that includes one or more adrenoceptor antagonists to the subject. In some embodiments, two or more types of adrenoceptor antagonists are provided separately. In some embodiments, the neurodegenerative condition is selected from the group consisting of iPD, AD, and MSA. In some embodiments, the neurodegenerative condition is any of the neurodegenerative conditions listed herein. In some embodiments, the composition includes a β1/β2- and/or α1/α2-receptor antagonist. In some embodiments, one or more of the adrenoceptor antagonists are β-blockers. In some embodiments, the adrenoceptor antagonists can include but are in no way limited to one or more of the following: acebutolol, betaxolol, bisopropolol, bopindolol, carvedilol, metoprolol, oxprenolol, propranolol, timolol, and combinations thereof. In an embodiment, the adrenoceptor antagonist used in the inventive method is carvedilol. In a preferred embodiment, the neurodegenerative condition is iPD, and at least one beta blocker is provided to the subject. In a preferred embodiment, at least one of the beta-blockers provided to the subject with iPD is carvedilol. One of skill in the art would readily appreciate that racemic mixtures, optical isomers, analogs, derivatives, and salts of each of the aforementioned substances could be used in the inventive methods. Furthermore, immediate-release as well as sustained-release preparations can be used with the inventive methods.

In some embodiments, the therapeutic compositions described above are provided in conjunction with, prior to, or after treatment with traditional dopaminergic therapies, including those described in the examples set forth herein. The compositions used in the inventive methods described herein can be provided at each and every stage of the neurodegenerative diseases described herein. For example, one or more adrenoceptor antagonists can be provided during any recognized stage of iPD, including the very early stages described herein. Compositions used in the inventive methods can also be provided prophylactically to an individual believed to have an elevated risk of developing any of the conditions described herein, compared to an average individual. In some embodiments, the individual is a mammal. In some embodiments, the individual is a human.

In various embodiments, one or more compounds or compositions described herein may be provided as a pharmaceutical composition, including a pharmaceutically acceptable excipient along with a therapeutically effective amount of one or more of the compounds or compositions described herein. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions, suspensions, or other cosmetic products. They can also be in the form of microspheres or nanospheres or lipid vesicles or polymer vesicles or polymer patches and hydrogels allowing controlled release. These topical-route compositions can be either in anhydrous form or in aqueous form depending on the clinical indication.

The pharmaceutical compositions used in the inventive methods can also contain any pharmaceutically acceptable carrier. "Pharmaceutically acceptable carrier" as used herein refers to a pharmaceutically acceptable material, composition, or vehicle that is involved in carrying or transporting one or more compositions or molecules of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

In certain preferred embodiments, pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic composition (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a composition or molecule and adjusting the dosage accordingly. For additional guidance, see *Remington: The Science and Practice of Pharmacy* (Gennaro ed. 20th edition, Williams & Wilkins Pa., USA) (2000).

Typical dosages of an effective amount of any of the adrenoceptor antagonists described herein can be as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method. The specific dosages and dosage ranges described herein below are for the treatment and prevention of any of the neurodegenerative diseases described herein, including iPD.

In some embodiments, a therapeutic dosage range of acebutolol is between 100 and 200 mg/70 kg every 10-12 h, when administered via the enteral route to treat or prevent any neurodegenerative condition described herein. In a preferred embodiment, the oral dosage of acebutolol needed to treat or prevent iPD motor and non-motor symptoms is 100 mg/70 kg every 6 h.

In some embodiments, a therapeutic dosage range of betaxolol is between 10 and 20 mg/70 kg every 10-12 h, when administered via the enteral route to treat or prevent any neurodegenerative condition described herein. In a preferred embodiment, the oral dosage of betaxolol needed to treat or prevent iPD motor and non-motor symptoms is 5 mg/70 kg every 6 h.

In some embodiments, a therapeutic dosage range of bisopropolol is between 5 and 10 mg/70 kg every 10-12 h, when administered via the enteral route to treat or prevent any neurodegenerative condition described herein. In a preferred embodiment, the oral dosage of bisoprolol needed to treat or prevent iPD motor and non-motor symptoms is 2.5 mg/70 kg every 6 h.

In some embodiments, a therapeutic dosage range of carvedilol is between 12.5 and 25 mg/70 kg every 10-12 h, when administered via the enteral route to treat or prevent any neurodegenerative condition described herein. In a preferred embodiment, the oral dosage of carvedilol needed to treat or prevent iPD motor and non-motor symptoms is 6.25 mg/70 kg every 6 h, or 10 mg/day using the controlled-release form.

In some embodiments, a therapeutic dosage range of metoprolol tartrate is between 100 and 200 mg/70 kg every 10-12 h, when administered via the enteral route to treat or prevent any neurodegenerative condition described herein. In a preferred embodiment, the oral dosage of metoprolol tartrate needed to treat or prevent iPD motor and non-motor symptoms is 50 mg/70 kg every 6 h.

In some embodiments, a therapeutic dosage range of oxprenolol is between 160 and 320 mg/70 kg every 10-12 h, when administered via the enteral route to treat or prevent any neurodegenerative condition described herein. In a preferred embodiment, the oral dosage of oxprenolol needed to treat or prevent iPD motor and non-motor symptoms is 80 mg/70 kg every 6 h.

In some embodiments, a therapeutic dosage range of pindolol is between 5 and 10 mg/70 kg every 10-12 h, when administered via the enteral route to treat or prevent any neurodegenerative condition described herein. In a preferred embodiment, the oral dosage of pindolol needed to treat or prevent iPD motor and non-motor symptoms is 2.5 mg/70 kg every 6 h.

In some embodiments, a therapeutic dosage range of propanolol is between 60 and 80 mg/70 kg every 10-12 h, when administered via the enteral route to treat or prevent any neurodegenerative condition described herein. In a preferred embodiment, the oral dosage of propanolol needed to treat or prevent iPD motor and non-motor symptoms is 40 mg/70 kg every 6 h.

In some embodiments, a therapeutic dosage range of timolol is between 10 and 20 mg/70 kg every 10-12 h, when administered via the enteral route to treat or prevent any neurodegenerative condition described herein. In a preferred embodiment, the oral dosage of timolol needed to treat or prevent iPD motor and non-motor symptoms is 5 mg/70 kg every 6 h.

In some embodiments, a therapeutic dosing regimen of one or more beta blockers for a subject with iPD is one which results in a resting heart rate of about 80 or fewer beats per minute. In some embodiments, a therapeutic dosage regimen for a subject with iPD is one which results in a resting heart rate of about fewer than 78 beats per minute, or fewer than 76 beats per minute, or fewer than 74 beats per minute, or fewer than 72 beats per minute, or fewer than 70 beats per minute, or fewer than 68 beats per minute, or fewer than 66 beats per minute.

In various embodiments, the invention teaches a method for determining whether or not iPD is progressing in a subject. In some embodiments, the method includes (1) performing an initial assay to measure cardiac uptake of iodine-123-metaiodobenzylguanidine ($^{123}$I-MIBG) in a subject suspected of having or having been diagnosed with iPD; and (2) subsequently performing an additional assay to measure cardiac uptake of $^{123}$I-MIBG in the subject, wherein iPD is determined to be progressing in the subject if the cardiac uptake of $^{123}$I-MIBG has decreased in the additional assay, compared to the initial assay; and wherein iPD is determined to not be progressing in the subject if the cardiac uptake of $^{123}$I-MIBG has not decreased in the additional assay, compared to the initial assay. In some embodiments, the cardiac uptake of $^{123}$I-MIBG is determined by $^{123}$I-MIBG myocardial scintigraphy, as normally performed by one of skill in the art. Non-limiting examples of applicable methods are described in Courbon et al. *Movement Disorders* Vol. 18, No. 8, 2003, pp. 890-897; Oka et al. *J Neural Transm* (2011) 118:1323-1327; and Navarro-Otano et al. *Parkinsonism and Related Disorders* 20 (2014) 192-197. In certain embodiments, a composition comprising an adrenoceptor antagonist (including one or more beta-blocker described herein) is administered to the subject in the time between the initial and subsequent assays. In various embodiments, the adrenoceptor antagonist can include, but is in no way limited to acebutolol, betaxolol, bisopropolol, bopindolol, carvedilol, metoprolol, oxprenolol, propranolol, and timolol.

In various embodiments, the invention teaches a method for diagnosing the presence or absence of iPD in a subject suspected as having iPD. In some embodiments, the method includes: performing an assay to measure cardiac uptake of $^{123}$I-MIBG in a subject suspected of having iPD, and diagnosing the subject as having iPD if the cardiac uptake of $^{123}$I-MIBG is less than that of a subject who does not have iPD; and diagnosing the subject as not having iPD, if the cardiac uptake of $^{123}$I-MIBG is not less than that of a subject who does not have iPD. In some embodiments, the cardiac uptake of $^{123}$I-MIBG is measured by $^{123}$I-MIBG myocardial scintigraphy, as normally performed by one of skill in the art. In some embodiments, the subject is diagnosed with iPD if the measured cardiac uptake of $^{123}$I-MIBG in the subject is about the same as that of a subject with iPD at any stage. In some embodiments, the subject is diagnosed as having a particular stage of iPD known to be associated with the measured level of cardiac uptake of $^{123}$I-MIBG.

The present invention also teaches a kit directed to one or more of: treating, inhibiting, promoting the prophylaxis of, alleviating the symptoms of, and reducing the likelihood of neurodegenerative diseases (such as any of those described herein), in a mammal in need thereof. The kit is an assemblage of materials or components, including at least one of the inventive compounds or compositions described herein. Thus, in some embodiments the kit contains a composition including one or more adrenoceptor antagonists. In some embodiments, one or more of the adrenoceptor antagonists are β-blockers. In some embodiments, the adrenoceptor antagonists can include but are in no way limited to one or more of the following: acebutolol, betaxolol, bisopropolol, carvedilol, metoprolol, oxprenolol, pindolol, propranolol, timolol, and combinations thereof. In an embodiment, the adrenoceptor antagonist included in the inventive kit is carvedilol. One of skill in the art would readily appreciate that racemic mixtures, optical isomers, analogs, derivatives, and salts of each of the aforementioned substances could be included in the inventive kit. Furthermore, immediate-release and sustained-release preparations can be included in the inventive kit.

The exact nature of the components configured in the inventive kit depends on its intended purpose. By way of non-limiting examples, some embodiments are configured for one or more purpose selected from: treating, inhibiting, promoting the prophylaxis of, alleviating the symptoms of, and/or reducing the likelihood of one or more neurodegenerative conditions described herein, including iPD. In one embodiment, the kit is configured particularly for the purpose of treating mammalian subjects. In another embodiment, the kit is configured particularly for the purpose of treating human subjects. In another embodiment, the kit is configured for treating adolescent, child, or infant human subjects. In further embodiments, the kit is configured for veterinary applications, treating subjects such as, but not limited to, farm animals, domestic animals, and laboratory animals.

Instructions for use can be included in the kit. "Instructions for use" typically include a tangible expression describing the technique to be employed in using the components of the kit to effect a desired outcome, such as treating, inhibiting, promoting the prophylaxis of, alleviating the symptoms of and/or reducing the likelihood of, or inhibiting a neurodegenerative condition described herein, including iPD, using the appropriate compositions and methods described herein. Optionally, the kit also contains other useful components, such as, diluents, buffers, pharmaceutically acceptable carriers, syringes, catheters, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions, molecules and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be one or more glass vials or plastic containers used to contain suitable quantities of an inventive composition disclosed herein. The packaging material generally has an external label which indicates the contents and/or purpose of the kit and/or its components.

One skilled in the art will recognize many methods and materials similar or equivalent to those described herein, which could be used in the practice of the present invention. Indeed, the present invention is in no way limited to the methods and materials described.

EXAMPLES

Example 1

Background

By way of additional background, iPD is a non-hereditary, chronic, and progressive neurodegenerative disorder of unknown etiology, characterized by the presence of bradykinesia (slowness of movements) associated with tremor at rest and/or muscle rigidity. iPD is typically associated with a significant loss of dopaminergic neurons in the substantia nigra pars compacta (SNpc). The SNpc provides dopaminergic innervation to the striatum, a brain structure mainly involved in the control of movements. It is estimated that the appearance of iPD motor symptoms does not occur until 50-80% of the dopaminergic neurons are lost.

The prevalence of iPD is approximately 1% in individuals over 65 years old. It is estimated that iPD affects almost 1.5 million people in the United States alone. In addition to characteristic motor symptoms, iPD is characterized by a number of "non-motor" symptoms, which add to the overall morbidity burden. Importantly, non-motor features may precede the diagnosis of iPD, sometimes by several years. They include autonomic (gastrointestinal dysfunction, cardiovascular dysfunction with orthostatic hypotension, urinary and sexual dysfunction, and hyperhidrosis), sleep (impaired sleep initiation and maintenance, rapid eye movement (REM) behavior disorder, and excessive daytime sleepiness), sensory (pain, hyposmia, and visual dysfunction), and/or neuropsychiatric disturbances (anhedonia, apathy, anxiety, depression, panic attacks, dementia, and psychosis).

It is important to consider that the above symptoms cannot be adequately explained by nigral pathology and dopaminergic deficiency and are generally not responsive to dopaminergic supplementation. Other extra-nigral dopamine unresponsive symptoms, occurring mostly in later stages of this disease, comprise postural instability and gait disorders, dementia and psychotic manifestations, although in some patients these last symptoms may also precede motor parkinsonism in DLB.

After reviewing extensive scientific literature, and considering their own clinical experiences, the inventors concluded that unresponsiveness to dopaminergic supplementation suggests that a mechanism different than primary nigral degeneration and dopaminergic deficiency may lie beneath the pathophysiology of the aforementioned symptoms. Specifically, as indicated above, the inventors concluded that a dysfunction of NE, another critical neurotransmitter circuitry in the nervous system, could explain most if not all the "non-motor" symptoms of the disease and play a critical role in the occurrence of the classical motors symptoms as well. The inventors believe that prolonged hyperactivity of adrenergic receptors, initially a physiological response to stress of various nature, can lead to accumulation of α-synuclein in a first (reversible) stage, and eventually to neuronal death. Importantly, while iPD is classically believed to be a disease of primary degeneration, based on the historical bias in favor of neuropathology as the diagnostic "gold standard," the inventors conclude that for many years iPD is a reversible process, testified by a multitude of non-motor symptoms related to the over activity of the noradrenergic system.

With all of these considerations in mind, the inventors determined that a subject could be evaluated for one or more of the above-listed early iPD symptoms, and if a diagnosis of early iPD is made, by using the methods of diagnosis described herein or otherwise, then the subject could be treated according to one or more of the inventive methods described herein.

Example 2

Current Treatment of Motor and Non-Motor Symptoms of iPD

As indicated above, despite all advances, iPD continues to be a progressive disorder for which no interventions are available to modify disease progression. Current treatment of iPD is only symptomatic and based mainly on dopaminergic supplementation, which temporarily improves motor impairment and quality of life. In certain embodiments, each of the following traditional treatment strategies could be used in conjunction with one or more of the inventive methods.

Dopaminergic Supplementation

Three main classes of dopaminergic agents are considered as first-line symptomatic therapies: monoamine oxidase B (MAO-B) inhibitors, dopamine agonists (DAs), and levodopa. MAO-B inhibitors (both rasagiline and selegiline) are a first line option for initial monotherapy in patients with mild disability. Although there is a suggestion that MAO-B inhibitors might be neuroprotective, there is no unequivocal proof for disease modification through either of the two available MAO-B inhibitors. DAs act directly upon dopamine receptors, mainly in the striatum, and are considered more efficacious on the cardinal motor features of iPD than MAO-B inhibitors, although a comparative trial has not been conducted. Non-ergolinic DAs (pramipexole, ropinirole, rotigotine and piribedil) are preferred among different DAs classes, because ergolinic DAs (cabergoline or pergolide) have shown pulmonary and cardiac valvular fibrotic reactions. In many national and international guidelines, DAs are recommended as a first-line therapy, particularly for young patients, because of a lower potential of DAs to induce motor complications (e.g. dyskinesias or response oscillations) as compared with levodopa. However, DAs efficacy on motor symptoms is lower than levodopa and patients started on DAs monotherapy will eventually need add-on levodopa as the disease progresses and motor symptoms become more severe. DAs are associated with more adverse effects (e.g. nausea, headache, leg edema, hallucinations, daytime somnolence and sleep attacks or orthostatic hypotension). Moreover, iPD patients treated with long-term DAs usually develop additional symptoms (not related to natural iPD history) including compulsive gambling, buying, sexual behavior, or eating, and commonly defined impulse control disorders. Historically, levodopa has been widely considered the most effective drug to treat the motor features of iPD and it is accepted as a first-line initial monotherapy in elderly patients in whom motor complication risk is generally low. Despite its efficacy, the risk of developing motor complications (which affect virtually all iPD patients after long term levodopa treatment) represents the principal reason to consider alternative dopaminergic therapies as initial monotherapy in iPD. Long-term motor complications, however, indicate that nondopaminergic systems are associated with the progression of the disease and could be a good target for disease modifying treatment.

Non-Dopaminergic Agents

Non-dopaminergic therapies have a little or absent role in the current treatment guidelines. Non-motor symptoms are not only frequent, but also often under-reported by patients and caregivers. Further, as they are frequently under-recognized by clinicians, they remain consequently under-treated. Moreover, the treatment merely addresses single or multiple symptoms (e.g. constipation, sleep disturbances, mood disorders, and autonomic dysfunction) in the same way as non iPD patients because they are considered "accidental" features associated with the fundamental movement disorder based on a dopaminergic deficit.

In summary, the previously unmet medical needs of iPD are: (a) unknown cause; (b) progressive worsening of all clinical features, including motor (tremor, bradykinesia, and rigidity) and non-motor (autonomic dysfunction, sleep disturbance, depression, fatigue, apathy, anxiety, and progressive cognitive decline) symptoms; (c) advanced motor complications, often associated with chronic dopaminergic supplementation (involuntary movements such as dyskinesia or dystonia, balance impairment, postural disturbance, and unpredictable immobility such as freezing of gait or prolonged "off" states); and (d) inadequate tremor control in many cases.

The inventors believe that some, if not all, of these unmet needs are related to the various roles of NE in the brain, and blocking or modulating NE neurotransmission could improve the motor and non-motor problems and protect against their progression in patients suffering from or susceptible to developing iPD.

Example 3

Rationale for Therapeutic Approach

As indicated above, iPD is currently considered a progressive neurodegenerative disease caused by the unexplained and premature death of dopaminergic neurons in the substantia nigra pars compacta (SNc), which are classically found to accumulate abnormal protein aggregates, rich in α-synuclein and ubiquitin, called Lewy bodies. However, a number of frequent, well-documented clinical and pathological features of iPD are not explained by the dopaminergic theory centered on the degeneration of the SNc. Numerous non-motor symptoms, which are levodopa unresponsive and unrelated to dopaminergic mechanisms, frequently occur in iPD, often causing more disability than the classical (dopaminergic) motor symptoms. Importantly, several non-motor symptoms appear to precede motor symptoms by many years, even up to two decades or more. In addition, Lewy bodies, the pathological marker of iPD, are not exclusively of the SNC, but have been found in many other cerebral and extra-cerebral locations, a finding that is considered by many experts to be a marker of the progression of the disease. The mechanism of formation of Lewy bodies, the pathological marker of iPD, was previously unknown. In particular, it was unclear what led to the abnormal α-synuclein aggregates that characterize the neurons affected by the disease. Finally, while the initial stages of the motor symptoms of iPD are responsive to dopaminergic supplementation (i.e. levodopa), the pre-motor symptoms and most importantly the symptoms marking the progression of the disease (i.e. postural instability, cognitive decline, motor fluctuations, and dyskinesias) are not affected by treatment with dopaminergic drugs.

Other structures, in addition to the nigrostriatal system, are involved in the neurodegenerative process that characterizes the progression of iPD. Autopsy-based studies have confirmed that α-synuclein Lewy pathology develops progressively in many nuclei and there is a particular loss of NE neurons of the locus coeruleus (LC) in patients with post-mortem diagnosis of sporadic iPD, as well as in individuals with incidental (prodromal or premotor) Lewy body disease, but not in age and gender matched controls. Abnormal noradrenergic function in iPD can be correlated with several of the non-motor symptoms, including: depression, REM-sleep disorder, and autonomic dysfunction. In fact, it appears that the contribution of the noradrenergic system in iPD dysfunction very likely explains many of the early non-motor symptoms of the disease.

Example 4

"Premotor" Parkinson's Disease

Most clinicians and researchers would agree on the likely existence of the premotor phase of iPD, based on clinical, pathologic, and epidemiologic studies. According to the so-called "Braak hypothesis," there are six chronologically different iPD stages, based on the progressive accumulation of Lewy bodies in the central nervous system. Synucleinopathic involvement of the SNc, considered the key event for the occurrence of motor Parkinsonism, does not become evident until stage 3. Extranigral loci, including the olfactory bulb, dorsal motor nucleus of the vagus nerve, and the LC appear to be affected before the SNc. α-synuclein immunoreactivity with Lewy neuritis followed by conspicuous Lewy bodies is seen in the hypothalamus, as well as in the pre- and postganglionic sympathetic and parasympathetic structures, such as in the enteric nervous system, cardiac and pelvic plexus, where this process might even start according to some experts.

Abnormal α-synuclein aggregation and Lewy bodies' formation in autonomic and noradrenergic structures explain all typical non-motor symptoms of iPD, and provide a mechanism to slow and potentially block the progression of the disease at a very early stage, by using the inventive methods.

Importantly, the current invention is partly based on the concept that over activity—and not degeneration—of the noradrenergic system is responsible for the early manifestations of iPD. The inventors believe that noradrenergic hyperactivity triggers non-motor symptoms and likely sustains progression of disease. Through the increased levels/activities of specific intracellular kinases, noradrenergic hyperactivity causes abnormal phosphorylation and aggregation of α-synuclein in all dopaminergic and non-dopaminergic efferent target neurons of the LC and the SNS. In fact, all of the structures involved in the progressive stages of the "Braak hypothesis" are efferent targets of LC or SNS.

The pathophysiological link between SNS hyperactivity and the development and progression of PD is the excessive activation of beta-1 adrenergic receptors in the target organs. In physiological conditions, G-coupled receptor kinases (GRKs) phosphorylate trans-membrane G receptors (including the beta-1 adrenergic receptor) de-sensitizing and down regulating them through the arrestin system, which ultimately leads to a reduced membrane density. In pathological conditions, excessive receptor stimulation induces a sharp increase of GRKs levels and activity, which on one hand reduces beta-1 adrenergic receptor membrane density, but on the other causes abnormal phosphorylation of alpha synuclein, which as a consequence aggregates forming the Lewy Bodies. Lewy Bodies typically start accumulating at the tip of the SNS axons (where the hyperactivity is maximal) and then spread antidromically to the cell body, which will eventually degenerate. The inventors believe it would be advantageous to block adrenergic over activation in the pre-motor phase of the disease, in order to prevent pathological accumulation of alpha-synuclein and the consequent development and progression of iPD.

To confirm the important role of the noradrenergic system, an early and specific extrastriatal sign of iPD is the impairment of the cardiac sympathetic system. The neuroimaging evidence for cardiac sympathetic "denervation" in iPD has been a watershed for the understanding of the mechanisms that underlie early disease symptoms and progression. Decreased cardiac uptake of iodine-123-metaiodobenzylguanidine ($^{123}$I-MIBG), a physiological analog of NE, has been reported in patients with iPD, and dementia with Lewy bodies (DLB). These imaging approaches are sensitive diagnostic tools that potentially differentiate iPD and DLB from other related disorders such as multiple system atrophy (MSA), progressive supranuclear palsy (PSP), corticobasal degeneration (CBD), Alzheimer's disease (AD) and parkin associated PD. In REM sleep behavior disorder (RBD), a condition considered highly predictive of iPD, $^{123}$I-MIBG cardiac uptake is similar to iPD. One hypothesis about the difference between the group of PD/DLB/RBD and other neurodegenerative diseases (MSA, PSP, CBD) is related to different kinds of gangliar neurodegeneration (post- in the first group and pre- in the second group). This finding suggests that cardiac sympathetic peripheral neurons might be affected in PD/DLB patients.

It is important to note, in support of the inventors' conclusions, that sympathetic cardioneuropathy, as measured by $^{123}$I-MIBG myocardial scintigraphy, is also characteristic of other common morbidities with recognized pathophysiological correlation to SNS impairment, explained as over-activity of the noradrenergic system. For example, a disparity between the neuronal release and the effective reuptake of NE in chronic heart failure (CHF) leads to an increased concentration of NE in the presynaptic cleft, causing a down-regulation of the myocardial β-adrenoceptors. In CHF patients, $^{123}$I-MIBG myocardial scintigraphy shows a reduced cardiac reuptake similar to that observed in iPD patients. The same scintigraphic results related to SNS hyperactivity are also commonly observed in hypertension, diabetes, and sleep apnea, which are all conditions significantly associated with iPD. In addition, patients with RBD show $^{123}$I-MIBG myocardial scintigraphy impairment that parallels iPD, and is explained as another example of neurodegeneration. However, patients with RBD and SA show lower $^{123}$I-MIBG levels than patients with RBD without SA, suggesting a common mechanism.

Importantly, treatment with beta-blockers has improved $^{123}$I-MIBG impairment in CHF patients. The inventors believe that treatment with beta-blockers could similarly improve cardiac dysautonomia in PD patients. In addition to $^{123}$I-MIBG myocardial scintigraphy, the inventors believe that beta-blockers will improve other cardiovascular dysautonomic symptoms, including orthostatic hypotension and heart rate variability.

Example 5

Other Autonomic Dysfunctions in Parkinson's Disease: the Example of Constipation In addition to cardiovascular dysautonomia, other autonomic dysfunctions are very common in patients with iPD, with a prevalence ranging from 14% to 80%. These symptoms further support the noradrenergic model, and can include gastrointestinal, urinary, sexual, and sudomotor dysfunction.

Constipation (less than three bowel movements per week) is the main gastrointestinal symptom seen in over 50% of iPD patients, preceding motor symptoms by many years and at least doubling the risk of iPD diagnosis. The enteric division of the autonomic nervous system is located in the plexus of Auerbach and of Meissner, containing cholinergic and opioidergic ganglionic cells. These cells, both sympathetically and parasympathetically innervated, and both sensitized by intestinal filling, regulate intestinal mucous secretion and peristaltic transport. In Parkinson's disease, Lewy bodies and α-synuclein deposits are evidenced not only in the vagal nerve and sacral nuclei as well as the enteric nervous system, but also in central parasympathetic structures (Barrington's defecation center).

Sensitized by intestinal filling, pressure waves are initiated by parasympathetic vagal (upper intestine) and pelvic (lower intestine) stimulation of the Auerbach's myenteric and Meissner's submucous plexus (facilitated by serotonin and inhibited by dopamine), and in the lower intestine, these pressure waves are inhibited by the noradrenergic sympathetic hypogastric nerve. Therefore, noradrenergic hyperactivity would explain the reduction of pressure waves, in particular after eating, when food inside the gut should activate the gastrocolic reflex.

Barrington's defecation center is strictly related to the LC. The LC-noradrenergic system is activated by visceral stimuli such as colon and bladder distension. Neurons of Barrington's nucleus (the pontine micturition center) which project to both the LC and preganglionic column of the lumbosacral spinal cord have been identified. The increase in LC discharge rate is often associated with activation of the forebrain electroencephalogram, indicating that the magnitude of LC activation produced by these stimuli is sufficient to impact forebrain targets. LC activation by physiological stimuli may be important in initiating a forebrain response that occurs in parallel with autonomic responses to these physiological stimuli. In an animal model, colonic distension increased the LC firing rate. In rats with lesions of Barrington's nucleus caused by ibotenic acid, increasing LC activation by colonic distension was significantly reduced, confirming a pivotal role of this nucleus in regulating brain noradrenergic system hyperactivation.

In wild type (WT) rats, electrical stimulation (5-20 Hz) of the cervical vagus elicited significant contractions in the mid colon and distal colon, whereas less pronounced contractions were observed in the proximal colon. Parasympathetic pelvic nerve stimulation elicited significant contractions in the rectum as well as the mid colon and distal colon. A parasympathetic antagonist (atropine) abolished the contractions induced by vagus nerve and pelvic nerve stimulation. On the other hand, sympathetic hypogastric nerve stimulation caused relaxations in the rectum, mid colon and distal colon and beta-blocker (propanolol) abolished the relaxations induced by hypogastric nerve stimulation.

Currently, basic treatment of constipation in Parkinson's disease includes dietary fiber, osmotic laxatives such as polyethylene glycol (PEG) (17 g/day) or lactulose (10-40 g/day), and psyllium preparations, in combination with physical exercise and adequate hydration.

Cholinomimetics (e.g. pyridostigmine bromide), peripheral dopamine antagonists (e.g. domperidone), 5-HT-4 receptor agonists (e.g. cisapride or mosapride), and the prostaglandin misoprostol, are also reported effective to treat constipation, whereas dopaminomimetic drugs may be helpful in lower intestinal and anorectal function. As demonstrated herein, and especially in the ensuing examples, beta-blockers reducing noradrenergic hyperactivity can improve gastrointestinal motor dysfunction and reduce constipation in iPD patients.

Example 6

Data Regarding Constipation

The following case report of unexpected relief of bothersome constipation, abdominal bloating and pain by treatment with carvedilol in one Parkinson's disease patient, triggered the subsequent analysis of patient data reported herein.

Case Report

A pleasant 54 year old left-handed female presented with a 12-month history of right hand tremors at rest associated with muscle pain of the right shoulder. Later on, she started dragging her right leg, tripping occasionally. Diagnostic workup included a brain and C-spine MRI with normal results. Voice, swallowing and handwriting were unaffected, but her ability to type with her right hand slowly deteriorated. Some ADLs, including dressing and blow drying her hair became progressively slower and more clumsy. Her non-motor symptoms initially included hyposmia, "acting out dreams" and anxiety. At initial encounter, there was no constipation, orthostatic dizziness, urinary frequency, sleep fragmentation, depression or cognitive decline. There was a history of mild concussion 7 years before symptom onset but no exposure to neuroleptics. The patient grew up on a farm and was possibly exposed to pesticides. The patient was initially started on dopamine agonist (pramipexole at doses up to 1.5 mg TID), which she tolerated well and partially controlled her tremor. One year later, due to persistent bradykinesia and rigidity of her right side, a small dose of levodopa (Sinemet 25/100 TID) was added with almost complete resolution of motor symptoms. During this time, she also developed constipation, sleep fragmentation and worsening anxiety. Low-dose beta-blocker therapy (carvedilol 6.25 mg BID) was started to treat anxiety avoiding the sedative effect of benzodiazepine. Her anxiety, constipation and sleep all improved dramatically. However, she self-discontinued carvedilol after completing the first month of therapy because "she was taking too many pills." At next follow-up, she reported the return of bothersome abdominal bloating and constipation. Carvedilol was restarted at the same dose with virtually immediate resolution of GI symptoms.

Patient Data Analysis

The inventors conducted a retrospective, cross-sectional medical record analysis of 333 consecutive patients with a diagnosis of iPD seen in the Movement Disorders clinic of Cedars-Sinai Medical Center from October 2010 to March 2014. Demographic and clinical data, including vitals, motor and non-motor symptoms, dopaminergic medications, comorbidities and anti-hypertensive medications were collected at the initial consultation visit. All data were collected in an Excel database and analyzed by SPSS version 19.0 (SPSS, Inc., Chicago, Ill.). Continuous variables were expressed as mean±standard deviation and compared by the use of Student t test (normally distributed) or as median±interquartile range value and compared by the use of Mann-Whitney U test (not normally distributed), as appropriate. Normality of data distribution was evaluated using the Kolmogorov-Smirnov test. Categorical variables were expressed as proportion and compared by use of $\chi2$ test with risk ratios and 95% confidence intervals quoted. To determine the independent predictors of constipation, logistic regression analysis was performed. Variables achieving $p<0.1$ on univariate analysis were then included in a multivariate analysis. Statistical significance was accepted at $p<0.05$.

TABLE 1

Characteristics of Study Cohort

| Demographic and clinical data | |
| --- | --- |
| Age, mean ± SD | 68.5 ± 7.5 |
| Gender male, n (%) | 214 (64.3) |
| PD duration, mean ± SD | 7.4 ± 5.8 |
| Tremor-like PD, n (%) | 234 (70.3) |
| PD treatment | |
| Levodopa, n (%) | 228 (68.5) |
| Dopamine Agonists, n (%) | 102 (30.6) |
| MAO-I, n (%) | 100 (30) |
| Amantadine, n (%) | 34 (10.2) |
| Anticholinergics, n (%) | 24 (7.2) |
| Other medications | |
| ACE-I/ARBs, n (%) | 73 (21.9) |
| Calcium Channel Blockers, n (%) | 28 (8.4) |
| Beta-blockers, n (%) | 63 (18.9) |
| Diuretics, n (%) | 37 (11.1) |
| Comorbidities | |
| pre-Hypertension, n (%) | 108 (32.4) |
| Hypertension, n (%) | 128 (38.3) |
| Diabetes Mellitus, n (%) | 28 (8.4) |
| Atrial fibrillation, n (%) | 32 9.6) |

Significantly, 203/327 patients (62.1%, 6 missing values) reported constipation, defined as the presence of constipation in the medical records or the use of drugs to treat constipation or patient report of infrequent bowel movement, subjective complaint of straining at stooling, incomplete evacuation, and abdominal bloating. Constipation was strongly associated with dopaminergic treatment. On the other hand, only 28/63 (44.4%) patients treated with beta-blockers reported constipation (Table 2).

TABLE 2

Reported Constipation in Cohort

| | Constipation | No Constipation | p value |
| --- | --- | --- | --- |
| Betablockers | 28 (44.4%) | 35 (55.6%) | 0.002 |
| No Betablockers | 174 (66.2%) | 89 (33.8%) | |

TABLE 3

Logistic Regression Univariate and Multivariate Analyses

|  | β | Wald | OR | 95% CI OR Lower | 95% CI OR Upper | p value | β | Wald | OR | 95% CI OR Lower | 95% CI OR Upper | p value |
|---|---|---|---|---|---|---|---|---|---|---|---|---|
| Age | .932 | 8.575 | 1.033 | 1.011 | 1.056 | .003 | .035 | 8.038 | 1.035 | 1.011 | 1.060 | .005 |
| Gender | .078 | .106 | 1.061 | .677 | 1.724 | .745 | .117 | .203 | 1.124 | .677 | 1.865 | .652 |
| PD duration | .063 | 8.371 | 1.065 | 1.021 | 1.112 | .004 | .022 | .782 | 1.023 | .973 | 1.075 | .377 |
| FHz | .348 | 1.881 | 1.416 | .861 | 2.327 | .170 | — | — | — | — | — | — |
| Tremor | −.010 | .002 | .990 | .608 | 1.613 | .968 | — | — | — | — | — | — |
| Levodopa | .978 | 15.984 | 2.659 | 1.645 | 4.295 | .0001 | .731 | 5.775 | 2.077 | 1.144 | 3.769 | .018 |
| DA | .637 | 5.868 | 1.891 | 1.129 | 3.166 | .015 | .567 | 3.803 | 1.763 | 1.005 | 3.094 | .048 |
| MAO-IB | −.292 | 1.385 | .747 | .480 | 1.214 | .239 | — | — | — | — | — | — |
| Amantadine | .424 | 1.154 | 1.528 | .705 | 3.315 | .283 | — | — | — | — | — | — |
| Anticholinergics | .231 | .264 | 1.260 | .522 | 3.036 | .607 | — | — | — | — | — | — |
| ACE-I/ARBs | −.410 | 2.296 | .664 | .391 | 1.128 | .130 | — | — | — | — | — | — |
| Beta-Blockers | −.894 | 9.825 | .409 | .234 | .715 | .002 | −1.121 | 13.194 | .326 | .178 | .597 | .0003 |
| $Ca^{++}$ Antagonists | −.541 | 1.863 | .582 | .268 | 1.266 | .172 | — | — | — | — | — | — |
| Diuretics | −.176 | .241 | .838 | .415 | 1.695 | .624 | — | — | — | — | — | — |
| Pre-HTN | .086 | .124 | 1.090 | .674 | 1.765 | .725 | — | — | — | — | — | — |
| HTN | −.351 | 2.253 | .704 | .447 | 1.109 | .130 | — | — | — | — | — | — |
| DM | .648 | 2.054 | 1.912 | .788 | 4.640 | .152 | — | — | — | — | — | — |
| AF | −.046 | .014 | .955 | .447 | 2.043 | .906 | — | — | — | — | — | — |

In a multivariate logistic analysis on constipation, including age, gender, PD duration, use of levodopa, use of dopamine-agonists and use of beta-blockers, the odds ratio of having constipation was 2.077 (p=0.016) on levodopa and 1.763 (p=0.048) on dopamine agonists treatment, but decreased to 0.326 (p=0.0003) in patients treated with beta-blockers. None of the other anti-hypertensive drugs showed any correlation with the subjective report of constipation in this cohort.

pharmacological treatment, was not associated with increased risk of constipation. As discussed above, intestinal motility is regulated by the autonomic system and beta-blockers can positively modulate sympathetic input.

In reviewing the patient data, the inventors determined that in earlier iPD patients (approximately ≤5 years from iPD diagnosis) the disease severity, as measured by the UPDRS part III in ON, was lower in patients taking beta-blockers (10.29±4 versus 14.57±7 in patients without beta blockers, p value=0.04).

TABLE 4

Constipation and Heart rate: Interaction with Dopaminergic Drugs

|  | No Betablockers | | | | | Betablockers | | | | |
|---|---|---|---|---|---|---|---|---|---|---|
|  | No Constipation | | Constipation | | p value | No Constipation | | Constipation | | p value |
|  | n | % | n | % |  | n | % | n | % |  |
| No Dopaminergic treatment | 39 | 57.4% | 29 | 42.6% | <0.0001 | 12 | 85.7% | 2 | 14.3% | 0.027 |
| Levodopa only | 32 | 28.3% | 81 | 71.7% |  | 14 | 40.0% | 21 | 60.0% |  |
| DA agonist only | 4 | 20.0% | 16 | 60.0% |  | 1 | 60.0% | 1 | 60.0% |  |
| Levodopa + DA agonists | 14 | 22.6% | 48 | 77.4% |  | 8 | 66.7% | 4 | 33.3% |  |

TABLE 5

Constipation and Beta-blockers: Interaction with Heart Rate

|  | HR <80 bpm | | | | | HR ≥80 bpm | | | | |
|---|---|---|---|---|---|---|---|---|---|---|
|  | No Constipation | | Constipation | | p value | No Constipation | | Constipation | | p value |
|  | n | % | n | % |  | n | % | n | % |  |
| No Betablockers | 43 | 33.6% | 85 | 68.4% | .004 | 45 | 33.6% | 89 | 66.4% | .153 |
| Betablockers | 27 | 57.4% | 20 | 42.6% |  | 8 | 50.0% | 8 | 50.0% |  |

Importantly, young age and treatments with beta-blockers were associated with a lower risk of constipation in this PD cohort, while dopaminergic treatments appeared to increase risk of constipation. Disease duration, corrected for age and Also, in patients with disease duration >5 years, the inventors found that beta-blockers are associated with less forgetfulness and apparently less overall "non-motor" burden.

Example 7

Conclusions

As demonstrated herein, beta-blockers reduce the overstimulation of the noradrenergic system, and therefore can be used to improve autonomic dysfunction and associated non-motor symptoms in iPD patients, including constipation, bladder over-activity, sleep disorders, anxiety, hypertension, and others. In addition to providing symptomatic relief, beta-blockers could also slow the progression of the disease by reducing the accumulation of α-synuclein/Lewy bodies induced by LC/SNS hyperactivity. Reduced abnormal α-synuclein accumulation in Lewy bodies will ultimately decrease the rate of neuronal death and neurodegeneration over time.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for determining whether or not a non-motor symptom phase of idiopathic Parkinson's disease (iPD) is progressing in a human subject who has not been diagnosed with iPD based on motor symptoms, and who does not exhibit a motor symptom of iPD, but is exhibiting a non-motor symptom of iPD, comprising:
performing an initial assay to measure cardiac uptake of iodine-123-metaiodobenzylguanidine ($^{123}$I-MIBG) in the subject;
administering a composition comprising one or more adrenoceptor antagonist selected from the group consisting of: acebutolol, betaxolol, bisopropolol, bopindolol, carvedilol, metoprolol, oxprenolol, propranolol, and timolol;
subsequently performing an additional assay to measure cardiac uptake of $^{123}$I-MIBG in the subject, wherein it is determined iPD is progressing in the subject if the cardiac uptake of $^{123}$I-MIBG has decreased in the additional assay, compared to the initial assay; and wherein it is determined iPD is not progressing in the subject if the cardiac uptake of $^{123}$I-MIBG has not decreased in the additional assay, compared to the initial assay; and continuing to administering the adrenoceptor antagonist if iPD is not progressing or providing an additional or alterative iPD treatment if iPD is progressing.

2. The method of claim 1, wherein the cardiac uptake of $^{123}$I-MIBG is measured by $^{123}$I-MIBG myocardial scintigraphy.

3. The method of claim 1, wherein the adrenoceptor antagonist is carvedilol.

4. A method for diagnosing a subject with the presence or absence of idiopathic Parkinson's disease (iPD) before the subject exhibits a motor symptom of iPD, comprising:
 performing an assay to measure cardiac uptake of iodine-123-metaiodobenzylguanidine ($^{123}$I-MIBG) in a subject;
 diagnosing the subject as having iPD if the cardiac uptake of $^{123}$I-MIBG is less than that of a subject who does not have iPD; and
 administering an adrenoceptor antagonist.

5. The method of claim 4, wherein the cardiac uptake of $^{123}$I-MIBG is measured by $^{123}$I-MIBG myocardial scintigraphy.

6. The method of claim 1, wherein the non-motor symptom of iPD is autonomic dysfunction, sleep related, sensory related, a neuropsychiatric disturbance or a combination thereof.

7. The method of claim 6, wherein the autonomic dysfunction is a gastrointestinal dysfunction, a cardiovascular dysfunction with orthostatic hypotension, urinary dysfunction, sexual dysfunction, hyperhidrosis or a combination thereof.

8. The method of claim 7, wherein the gastrointestinal dysfunction is constipation.

9. The method of claim 6, wherein the sleep related symptom is impaired sleep initiation and maintenance, rapid eye movement (REM) behavior disorder, excessive daytime sleepiness or a combination thereof.

10. The method of claim 6, wherein the sensory related symptom is pain, hyposmia, visual dysfunction or a combination thereof.

11. The method of claim 6, wherein the neuropsychiatric disturbance is anhedonia, apathy, anxiety, depression, panic attack, dementia, psychosis or a combination thereof.

12. The method of claim 4, wherein the adrenoceptor antagonist is carvedilol.

13. The method of claim 4, further comprising administering a dopaminergic agent to the subject.

14. The method of claim 4, wherein the adrenoceptor antagonist is selected from the group consisting of: acebutolol, betaxolol, bisopropolol, bopindolol, carvedilol, metoprolol, oxprenolol, propranolol, and timolol.

* * * * *